United States Patent [19]

Kirmann

[11] Patent Number: Plant 6,029

[45] Date of Patent: Sep. 29, 1987

[54] GERANIUM PLANT NAMED VICKY

[75] Inventor: Wolfgang Kirmann, Langenzersdorf, Austria

[73] Assignee: Mirko Vavra, Bisamberg, Austria

[21] Appl. No.: 811,168

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Vicky having salmon-pink flower color variegated with deep salmon-red on upper petals; medium early flowering; good bud production at night temperatures up to 16° C., thus providing a long and continuous flowering period; vigorous, self-branching growth habit; and ease of propagation and good rooting habit.

2 Drawing Figures

The present invention comprises a new and distinct cultivar of geranium, botanically known as *Pelargonium domesticum,* and hereinafter referred to by the cultivar name Vicky.

Vicky is a product of a planned breeding program which had the objective of creating new geranium cultivars having a compact growth habit with good branching, excellent flower production, early flowering and long flowering period, and salmon-pink flower color.

Vicky was originated from a hybridization made by applicant in a controlled breeding program in Bisamberg, Austria in 1981. The female parent was Aurora, a cultivar characterized by its pale salmon-pink flower color, very vigorous growth habit, late flowering but undesirable spreading growth habit.

The male parent of Vicky was a cultivar designated as seedling 78/75 having a compact growth habit, salmon flower color, and very good flower production.

Vicky was discovered and selected as one flowering plant within the progeny of the stated cross by applicant on Apr. 25, 1982, in a controlled environment in Bisamberg, Austria.

The first act of asexual reproduction of Vicky was accomplished when vegetative cuttings were taken from the initial selection on Aug. 31, 1981 in a controlled environment in Bisamberg, Austria by a technician working under formulations established and supervised by Wolfgang Kirmann. Horticultural examination of selected units initiated in the spring of 1982 has demonstrated that the combination of characteristics as herein disclosed for Vicky are firmly fixed and are retained through successive generations of asexual reproduction.

Vicky has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Vicky, which in combination distinguish this geranium as a new and distinct cultivar.

1. Salmon-pink flower color, variegated with salmon-red on upper petals.

2. Propagates well, with very good rooting habit.

3. Medium early flowering and long flowering period.

4. Vigorous, self-branching growth habit resulting in the setting of many buds.

5. Buds are produced under normal greenhouse conditions (5000 Lux for 16 hours per day) at 14°–16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.

6. Vicky is unique with regard to the combined features of compactness, continuous flowering, floriferous habit, and salmon-pink flower color.

Of the many commercial cultivars known to the present inventor, the most similar in comparison to Vicky is Aurora, an unpatented but commercial cultivar. In comparison to Aurora, Vicky has a more compact growth habit, flowers earlier, has larger flowers, and a more intense flower color.

The accompanying photographic drawings show typical flower and foliage characteristics of Vicky, with colors being as true as possible with illustrations of this type.

Sheet 1 is a perspective view of a potted plant of Vicky.

Sheet 2 is a black and white print showing the upper surface of immature and mature plants of Vicky.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

Classification:

*Botanical.*—*Pelargonium domesticum.*

*Commercial.*—Commonly referred to as a "Martha Washington" geranium, and having the cultivar name Vicky.

INFLORESCENCE

A. Umbel:

*Average diameter.*—Very large, 140–150 mm.

*Peduncle length.*—Normal.

*Pedicel length.*—Normal.

B. Corolla:

*Average diameters.*—80–90 mm; total inflorescence diameter extends beyond foliage.

*Form.*—Five-six petals; symmetric.

*Color (general tonality from a distance of three meters).*—Salmon-pink with dark salmon-red variegation on the upper petals.

*Color (upper surface).*—55C-D variegated with 47B on the upper petals.

C. Bud:

*Shape.*—Elongated.

*Color.*—Salmon.

D. Reproductive organs:

*Androecium.*—Red-yellow.

*Gynoecium.*—Five-six lobed stigma.

E. Spring flowering response period: Medium early.

F. Durability: Very good.

PLANT

A. Foliage:

*Form.*—Zygomorphic with a nectar spur.

*Margin.*—Crenate with slight indentation.

*Color (upper surface).*—Light green.

*Tolerance of Botrytis and soil fungi.*—Very good.

B. General appearance and form:

*Internode length.*—Normal.

*Branching pattern.*—Excellent.

*Height.*—Medium compact.

I claim:

1. A new and distinct cultivar of geranium named Vicky, as described and illustrated, and particularly characterized by its salmon-pink flower color variegated with deep salmon-red on upper petals; medium early flowering; good bud production at night temperatures up to 16° C., thus providing a long and continuous flowering period; vigorous, self-branching growth habit; and by its ease of propagation and good rooting habit.

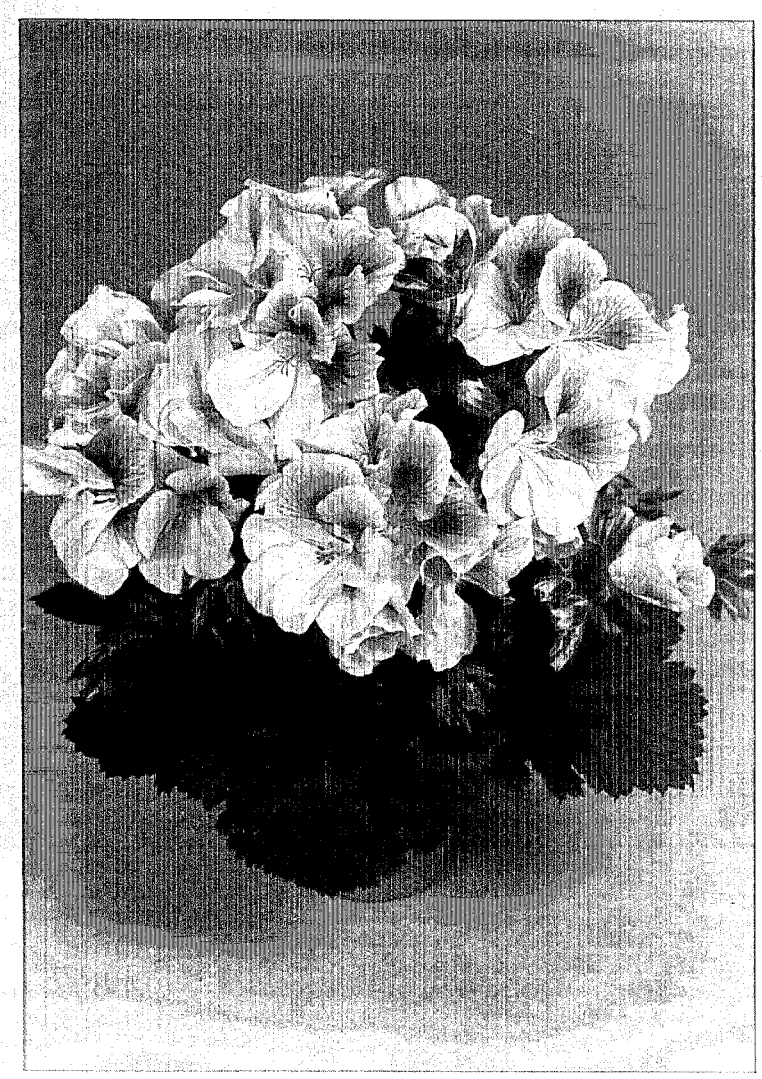

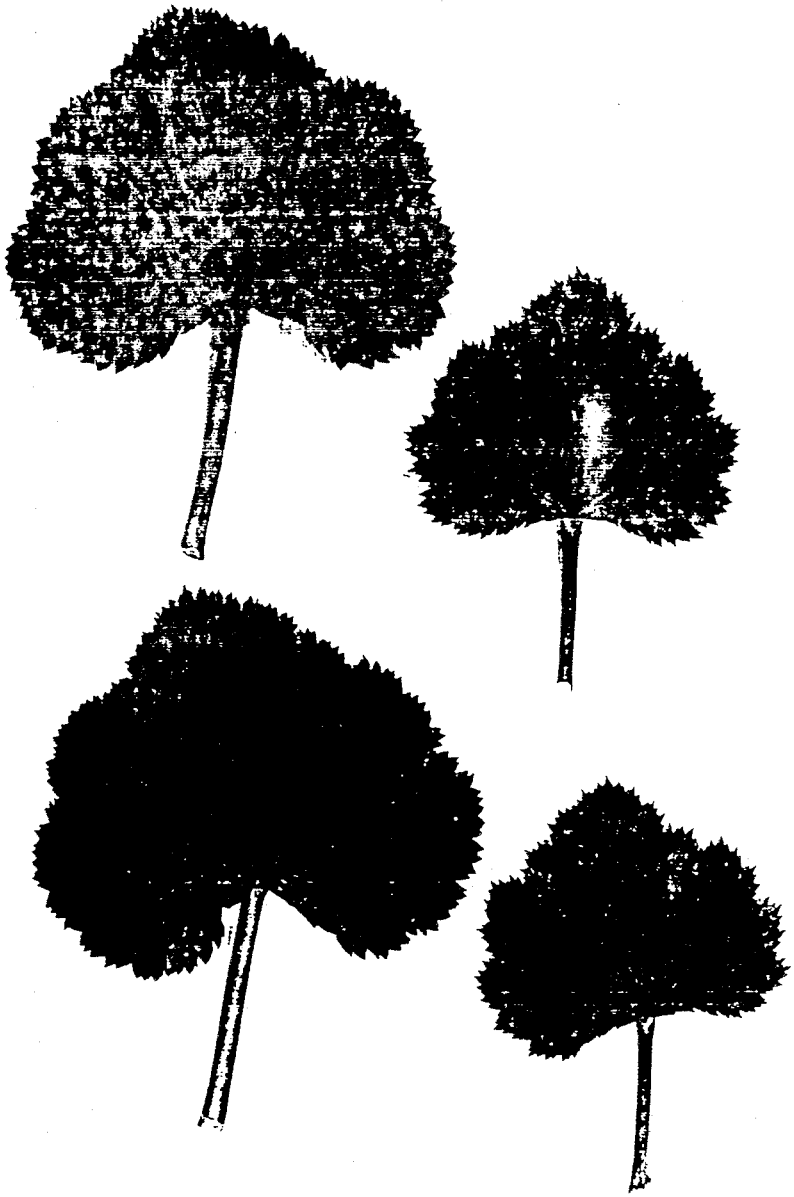

* * * * *